United States Patent [19]
Kolfenbach et al.

[11] Patent Number: 5,697,890
[45] Date of Patent: Dec. 16, 1997

[54] TONGUE DEPRESSOR

[76] Inventors: John J. Kolfenbach, 7220 River Forest La.; Michael J. Cichon, 9804 N. 56th St., both of Temple Terrace, Fla. 33617

[21] Appl. No.: 469,548

[22] Filed: Jun. 6, 1995

[51] Int. Cl.$^6$ .................................................. A61B 13/00
[52] U.S. Cl. .......................... 600/235; 600/239; 600/240
[58] Field of Search ........................... 600/239, 240, 600/241, 243, 246, 235, 237; D24/136

[56] References Cited

U.S. PATENT DOCUMENTS

| | | | |
|---|---|---|---|
| D. 185,100 | 5/1959 | Schlosser | 600/240 |
| D. 263,743 | 4/1982 | Priestman | D24/136 |
| 510,516 | 12/1893 | Nithack . | |
| 668,823 | 2/1901 | Pilling | 600/240 |
| 1,252,177 | 1/1918 | Redfield | 600/239 |
| 1,319,904 | 10/1919 | Roberts | 600/239 |
| 1,374,984 | 4/1921 | Cameron | 600/239 |
| 1,510,304 | 10/1924 | Cameron . | |
| 1,613,373 | 1/1927 | Beck | 600/240 |
| 3,162,191 | 12/1964 | Canan | 600/240 |
| 4,024,859 | 5/1977 | Slepyan et al. | 600/239 |

FOREIGN PATENT DOCUMENTS 000007872  1/1899  United Kingdom ................. 600/240

*Primary Examiner*—Richard J. Apley
*Assistant Examiner*—Glenn E. Richman
*Attorney, Agent, or Firm*—H. W. Oberg

[57] ABSTRACT

A tongue depressor with an elongate body having a tongue depressing end portion extending at a downward angle from the body and in the form of a ring with an aperture.

11 Claims, 2 Drawing Sheets

5,697,890

TONGUE DEPRESSOR

BACKGROUND OF THE INVENTION

The invention relates to a spatula for use during a medical-diagnostic inspection of the mouth and throat, but more particularly, the invention relates to a tongue depressor of preferably polymeric material for gently, downwardly depressing a tongue to minimize gagging.

The gagging reaction has been a persistent, continuing problem in the medical examination of the throat cavity. It has been a source of considerable discomfort to many of the physicians' patients.

The human tongue extends from an elevated arc area near the throat toward the tongue tip at the mouth. The arc area of the tongue must be depressed to obtain a good view of the throat. The sensitivity of the tongue is the highest at the arc near the base of the tongue and decreases toward the tip.

In many standard throat inspections, the tongue is protruded thrusting the sensitive area of the tongue forward and a spatula such as a flat wooden spatula is used to depress the arc of the tongue for viewing of a patient's throat.

Early tongue depressors were designed with a downwardly extending tongue retractor end portion to help retract the tongue while in a protruding position. Examples of such retractor devices appear in U.S. Pat. No. 412,409 to Osborn and U.S. Pat. No. 1,510,304 to Cameron. It has been found that examinations requiring protrusion of the tongue are very unpleasant and may cause a gagging because of the type of contact between the spatula and the sensitive area near the base of the tongue.

An improved spatula for inspecting the throat while depressing a tongue is disclosed in U.S. Pat. No. 3,890,960. The spatula has projecting prongs, as an integral part of a downwardly extending tongue depressing end portion. Choking or gagging is, to some degree, alleviated as the linearally extending prongs of the spatula reduce a pressure contact area with the base of the tongue at its highly sensitive area. A problem with depressors of this type is that the linearally extending prongs are along the axis of the spatula allowing unrestricted axial movements of the spatula relative to the tongue near the base area which can also introduce gagging. Also, the prongs may allow relative movement between the spatula and tongue when pressure is applied to the spatula.

A visual problem associated with spatulas is that of seeing around the spatula while examining a throat. To solve the visual problem, disposable spatulas such as that disclosed in the '960 patent, have been configured with a manual gripping portion in the form of a separate handle into which the disposable spatula must be inserted. One must always have a handle for attaching to the spatula to facilitate use. The use of a reusable handle in combination with a antiseptically clean spatula poses a risk of infection unless the handle is antiseptically cleaned after each use.

A very limited number of physicians have adopted a relaxed tongue method which involves depressing a non-protruding tongue by forcing the tongue down deeply by pressing down in the area of the tongue anterior to the arc, thus avoiding direct contact with the sensitive arc area. The procedure is somewhat difficult to employ using conventional wood depressors.

The physical properties of the tongue in the relaxed tongue method are quite different from the characteristics of the protruded, tense tongue. In particular, the tongue is quite flaccid and rests much lower in the mouth and is less sensitive to gagging. The tongue in this method rests easily in the mouth with the tip positioned against the inner side of the lower front teeth. The flaccid tongue is very easily depressed and draws the arc of the tongue downward when deeply depressed allowing an excellent view of the throat area while avoiding the troublesome gagging reaction. The sensitive arc area is never directly contacted.

This invention is directed to a disposable, low cost tongue depressor of the type for depressing a relaxed tongue.

SUMMARY OF THE INVENTION

In accordance with the invention, a disposable tongue depressor is provided which is preferably made of a suitable polymeric material. The depressor is of the type with an elongate body that is intermediate a tongue depressing end portion and an opposite end portion for manually gripping the depressor. The tongue depressing end portion extends at a downward angle from the elongate body and is in the form of a substantially flat ring forming an aperture. The manual gripping end portion of the depressor may be a straight extension of the elongate body, but optionally and preferably it extends downward at an angle from the body for contacting a palm of a user's hand. The downwardly extending manual gripping end helps position the depressor and a hand relative to a tongue for easy viewing of a throat. The substantially flat ring with its aperture eliminates (or substantially avoids) contact with sensitive areas of the tongue while also helping keep the depressor from sliding on a tongue when the depressor is in use.

An object of the invention is to provide a disposable tongue depressor that renders a medical-diagnostic inspection of the mouth and throat more pleasant for the patient by avoiding contact with the sensitive area of the tongue and inhibiting the depressor from sliding relative to the tongue.

Another object of the invention is to provide a depressor for examining the mouth and throat with a flaccid (relaxed) and non-protruding tongue.

An advantage of the invention is its simple use coupled with minimum patient discomfort and without gagging.

The features and other objects and advantages of the invention will be more apparent after reviewing the drawings and description thereof, wherein.

DESCRIPTION OF PREFERRED EMBODIMENT

Figure 1:
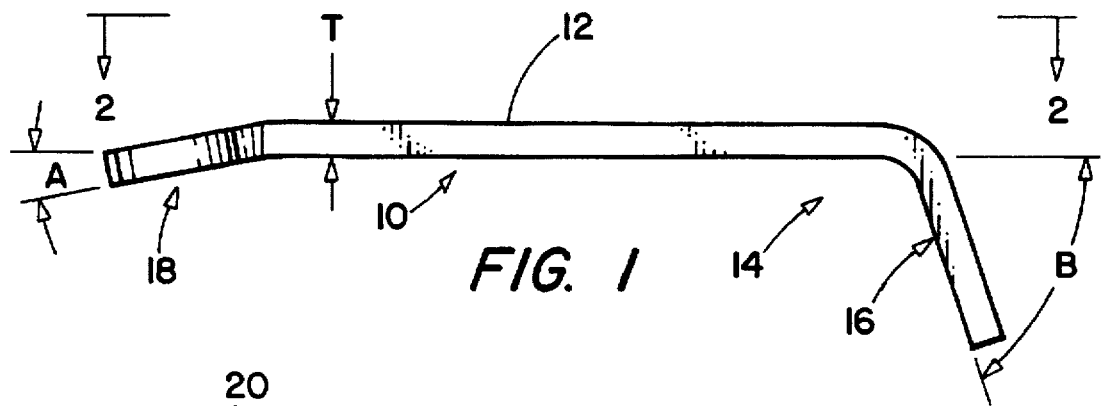
FIG. 1 is a side view of a tongue depressor of the invention.
Figure 2:
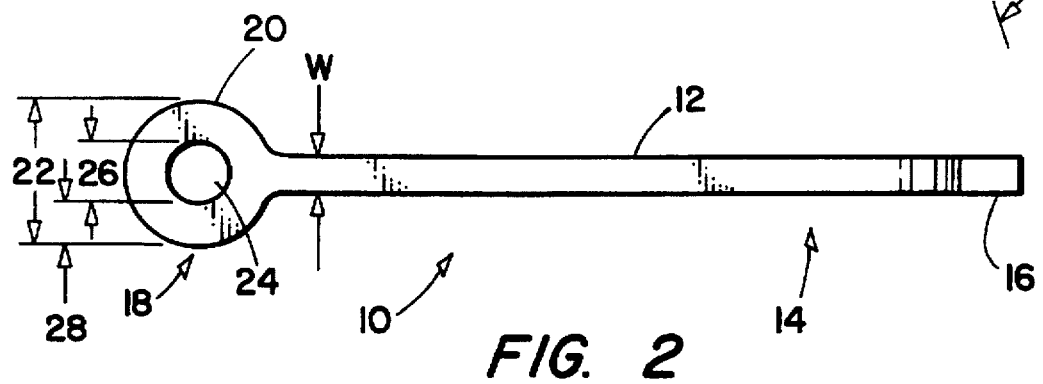
FIG. 2 is a top view of the depressor taken generally along the lines 2—2 of FIG. 1.

Referring primarily to FIGS. 1 and 2, the tongue depressor 10 of the invention has an elongate body 12 having a width W and thickness T. The body may be made of any suitable polymeric material that can be injection molded such as high densitypolyethylene. The width and thickness of the elongate body are sized to provide a requisite flexural modulus along a length L to facilitate depressing a flaccid tongue when the spatula is in use. A manual gripping end portion 14 integrally extends from the body 12 and optionally, but preferably, has a palm engaging part 16 that extends at a downward angle preferably from about 45 to about 90 degrees relative to the elongate body.

An enlarged tongue gripping portion 18 integral with the body extends at a downward angle A preferably from about 7 to 15 degrees. As particularly shown in FIG. 2, the enlarged tongue gripping portion is generally in the form of a flat ring 20 having a diametrical width 22. The ring forms an aperture 24 with a diametrical width 26. Optionally, the diametrical width W of the aperture 26 is greater than the width of the body near downward angle A, and at least two times the width W of the body.

The shape of the ring may be oval, elliptical, circular, square, rectangular or the like, but preferably, it is substantially circular as shown. Similarly, the shape of the aperture may be oblong, round, elliptical, square, rectangular and the like, but preferably is substantially circular whereby in conjunction with the diametrical width of the ring defines a rim width 28 of the ring. Preferably, the rim width 28 is at least equal to the width of the elongate body W with a downward angle A for sizing the ring for pressure contact with a tongue.

Figure 3:
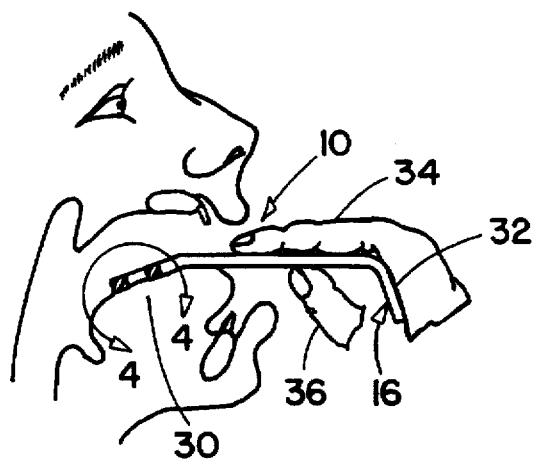
FIG. 3 is a schematical view showing the tongue depressor of the invention in use.
Figure 4:
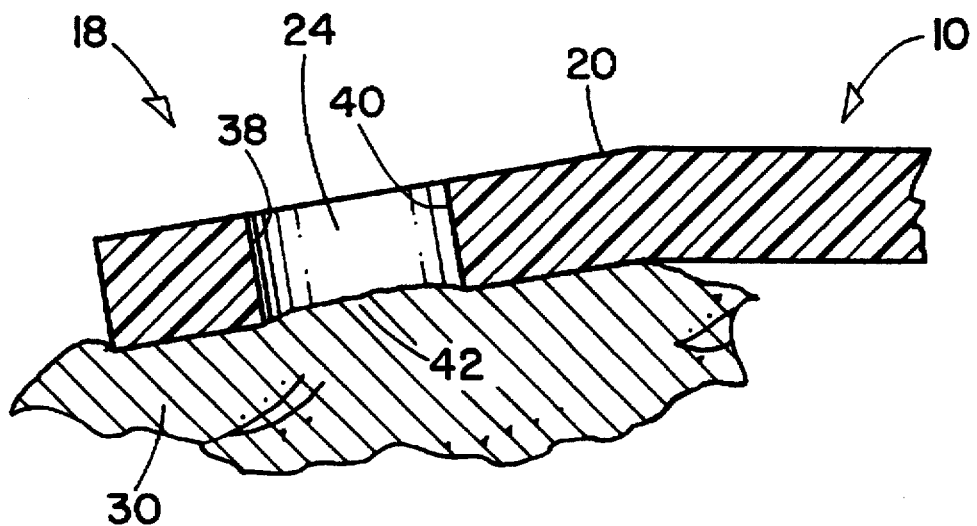
FIG. 4 is an enlarged partial view taken generally along the line 4—4 of FIG. 3; and, FIG. 5–7 are partial, schematical views similar to FIG. 2 but showing alternate embodiments of the invention.

Referring to FIGS. 3 and 4, when the tongue depressor 10 of the invention is in use, it is positioned in the mouth of a patient whose tongue 30 is in a relaxed (non protruding) position. The enlarged tongue gripping portion 18 is positioned near the base forward of the sensitive arc area. The palm engaging part 16 contacts the palm 32 of a user while an index finger 34 and thumb 36 are used to grip the depressor in a "pencil-like" gripping fashion. Of course, other convenient and comfortable gripping positions can be used depending on what is comfortable for a user. A slight downward pressure is applied to the depressor which pushes a flaccid or relaxed tongue downwardly for easy viewing of the patient's throat while avoiding a troublesome gagging reaction. The aperture 24 helps fix the depressor relative to the tongue and the enlarged tongue gripping portion increases surface contact with the tongue. Edges 38,40 of the ring 20 at the aperture gently contact the tongue helping keep the depressor from sliding in relation to the tongue. The tongue slightly protrudes 42 into the aperture anchoring the position of the tongue during depression.

Material properties and dimensions suitable for tongue depressors of the invention are listed below in Table 1:

TABLE 1

| Material | Plastic (eg high density polyethylene |
|---|---|
| Tensile strength, psi | 3000 (min) |
| Flexural modulus, psi | $1 - 3 \times 10^5$ |
| Elongate body | |
| length, in. | 3½ to 4¾ |
| width, in. | 3/16 to 7/32 |
| thickness, in. | 3/16 to 7/32 |
| Manual gripping end | |
| length, in. | ⅝ to 1½ |
| Tongue gripping end | |
| width - flat ring, in. | ¾ to 1 |
| width - aperture, in. | ⅜ to ⅝ |
| width - rim, in. | 3/16 to ¼ |
| angle to body, degrees | 7–15 |

ALTERNATE EMBODIMENTS OF THE INVENTION

Figure 5:
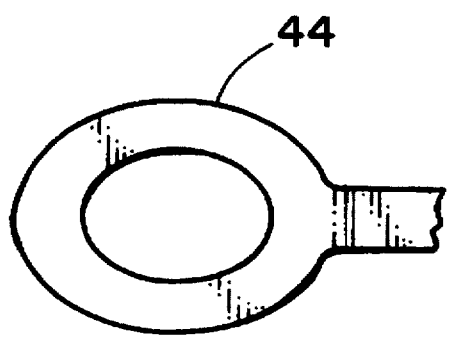
Figure 6:
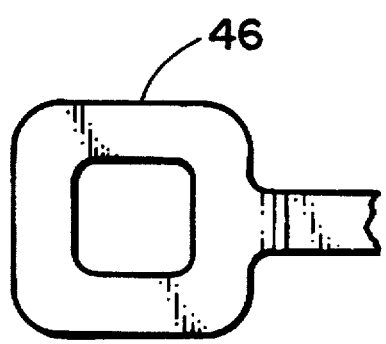
Figure 7:
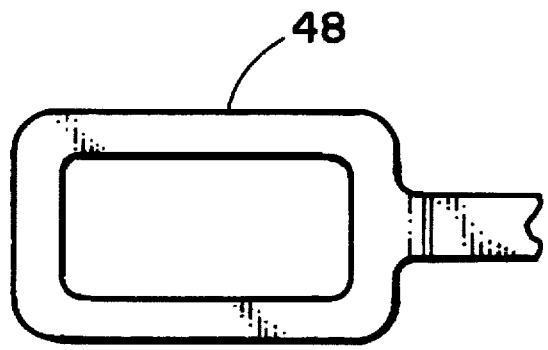

Referring to FIG. 5–7, other shapes for the enlarged tongue gripping portion are schematically illustrated. FIG. 5 illustrates a ring 44 having generally an elliptical or oblong shape. FIG. 6 illustrates a ring 46 having generally a square shape. FIG. 7 illustrates a ring 48 having generally a rectangular shape.

The foregoing detailed description is made for purpose of illustration only and is not intended to limit the scope of the appended claims.

What is claimed is:

1. In a tongue depressor of the type with an elongate body having width, and intermediate a manual gripping end portion and an enlarged tongue depressing end portion, said tongue depressing end portion extending at a downward angle from the body, the improvement comprising:

the tongue depressing end portion generally shaped as an open ring with a downward surface that defines a means for engaging a tongue and which helps keep the depressor from sliding on a tongue, the ring having 1) a width that is greater than the width of the body near the downward angle from the body and 2) an aperture with a width; and wherein the tongue depressing end portion extends at an angle from about 7 to 15 degrees relative to the elongate body.

2. The tongue depressor as claimed in claim 1 wherein the width of the ring is at least three times the width of the body.

3. The tongue depressor as claimed in claim 1 wherein the width of the aperture is greater than the width of the body near the downward angle from the body.

4. The tongue depressor as claimed in claim 3 wherein the ring and aperture are substantially circular.

5. The tongue depressor as claimed in claim 1 wherein the manual gripping end portion includes a part extending at a downward angle from the body and located for engaging the palm of a hand when the depressor is in use.

6. The tongue depressor as claimed in claim 1 wherein the difference between the width of the aperture and the width of the ring defines a rim width that is at least equal to the width of elongate body near the downward angle of the tongue depressing end portion.

7. The tongue depressor as claimed in claim 1 wherein the depressor is formed of a polymeric material.

8. The tongue depressor as claimed in claim 1 wherein the ring is substantially flat.

9. In a tongue depressor of the type with an elongate body having width, and intermediate a manual gripping end portion and an enlarged tongue depressing end portion, said tongue depressing end portion extending at a downward angle from the body, the improvement comprising:

the tongue depressing end portion extending downward at an angle from about 7 to 15 degrees and substantially shaped as a circular open ring with an encircling downward surface for engaging a tongue, the ring having a diametrical external width and an aperture with a diametrical width; and the manual gripping end portion includes a part extending at a downward angle from the body and located for engaging the palm of a hand when the depressor is in use.

10. The tongue depressor as claimed in claim 9 wherein the part of the manual gripping end that extends at a downward angle extends at an angle of about 45 to 90 degrees relative to the elongate body.

11. In a tongue depressor of the type with an elongate body having thickness, width, and intermediate a manual gripping end portion and an enlarged tongue depressing end portion, said tongue depressing end portion extending at a downward angle from the body, the improvement comprising:

the tongue depressor formed of a polymeric material having a flexural modulus of substantially $1-3 \times 10^5$ psi; and the tongue depressing end portion generally shaped as an open ring with a downward surface that defines a means for engaging a tongue and which helps keep the depressor from sliding on a tongue, the ring having 1) a width that is greater than the width of the body near the downward angle from the body and 2) an aperture with a width; and wherein the tongue depressing end portion extends at an angle from about 7 to 15 degrees to the elongate body which has a flexural modulus established by the polymeric material in conjunction with a width of substantially 3/16 to 7/32 inches and a thickness of substantially 3/16 to 7/32 inches.

* * * * *